US009422270B2

(12) United States Patent
Kwant et al.

(10) Patent No.: US 9,422,270 B2
(45) Date of Patent: Aug. 23, 2016

(54) MELAM GRANULATE MATERIAL AND PROCESS FOR PREPARATION THEREOF

(75) Inventors: Gerard Jan Kwant, Sittard (NL); Christiaan Johannes Cornelis Stoelwinder, Sittard (NL); Bas van Laarhoven, Maastricht (NL)

(73) Assignee: DSM IP ASSETS B.V., Heerlen (NL)

( * ) Notice: Subject to any disclaimer, the term of this patent is extended or adjusted under 35 U.S.C. 154(b) by 714 days.

(21) Appl. No.: 13/703,479

(22) PCT Filed: Jun. 7, 2011

(86) PCT No.: PCT/EP2011/059403
§ 371 (c)(1), (2), (4) Date: Mar. 4, 2013

(87) PCT Pub. No.: WO2011/154409
PCT Pub. Date: Dec. 15, 2011

(65) Prior Publication Data
US 2013/0210970 A1     Aug. 15, 2013

(30) Foreign Application Priority Data

Jun. 11, 2010 (EP) .................... 10165705

(51) Int. Cl.
| C07D 403/12 | (2006.01) |
| C08K 5/3492 | (2006.01) |
| B01J 2/16 | (2006.01) |
| B01J 2/30 | (2006.01) |
| C08J 3/03 | (2006.01) |
| C08J 3/12 | (2006.01) |
| C08J 3/20 | (2006.01) |
| C08K 9/08 | (2006.01) |

(52) U.S. Cl.
CPC ............. *C07D 403/12* (2013.01); *B01J 2/16* (2013.01); *B01J 2/30* (2013.01); *C08J 3/03* (2013.01); *C08J 3/122* (2013.01); *C08J 3/124* (2013.01); *C08J 3/203* (2013.01); *C08K 5/3492* (2013.01); *C08K 5/34922* (2013.01); *C08K 9/08* (2013.01)

(58) Field of Classification Search
None
See application file for complete search history.

(56) References Cited

U.S. PATENT DOCUMENTS

2006/0276572 A1    12/2006    Kierkels et al.

FOREIGN PATENT DOCUMENTS

EP    0 666 259    8/1995

OTHER PUBLICATIONS

International Search Report for PCT/EP2011/059403, mailed Jul. 6, 2011.

*Primary Examiner* — Nicole M Buie-Hatcher
(74) *Attorney, Agent, or Firm* — Nixon & Vanderhye P.C.

(57) ABSTRACT

The invention relates to a method for producing a free flowing flame retardant material, comprising steps of i. preparing an aqueous slurry from a freshly prepared moist melam having a water content of at least 8 wt. %, relative to the total weight of the moist melam, the slurry comprising water, melam and a water soluble polymeric binding agent, wherein the melam is present in an amount of 5-35 wt. % relative to the total weight of the slurry, and the water soluble polymeric binding agent is present in an amount of 0.5-8 wt. % relative to the total amount of melam and the water soluble polymeric binding agent; ii. drying the slurry in a fluid bed to form a granulate material; and iii. collecting the resulting granulate material. The invention also relates to a melam granulate material, obtainable by said process.

9 Claims, No Drawings

MELAM GRANULATE MATERIAL AND PROCESS FOR PREPARATION THEREOF

This application is the U.S. national phase of International Application No. PCT/EP2011/059403, filed 7 Jun. 2011, which designated the U.S. and claims priority to EP Application No. 10165705.4, filed 11 Jun. 2010, the entire contents of each of which are hereby incorporated by reference.

The invention relates to a method for producing a free flowing flame retardant material, in particular a melam based flame retardant material. The invention further relates to said free flowing flame retardant (FFFR) material, the use of the FFFR material in the preparation of polymer compositions, and to polymer compositions containing melam.

Melamine forms melamine condensation products when heated under certain reaction conditions. Ammonia is evolved in the reaction. Similarly, melamine salts form condensation products when heated. Melamine condensation products include melem, melone, and melam, as well as salts thereof. Generally, melam (C6H9N11) forms upon heating of melamine and/or melamine salts below 315° C. Melam is also formed as a by-product of melamine synthesis in very low amounts.

Laboratory scale processes relating to the preparation of melam via condensation are described in, for example, V. A. Gal'perin et al., Zhurnal Organicheskoi Khimii, Vol. 7, No. 11, pp. 2431-2432 (November 1971) and Gavrilova et al., Zhurnal Organicheskoi Khimii, Vol. 13, No. 3, pp. 669-670 (March 1977). More recently, in WO 96/16948 a commercial scale process is disclosed in which melamine condensation products, including melam, were produced through heating melamine or a melamine salt in the presence of: (i) at least one organic acid, (ii) at least one ammonia or melamine salt of the organic acid, or (iii), a mixture of (i) or (ii), under reaction conditions effective for the formation of the melamine condensation product. The condensation product was then washed with a 3% ammonia solution and dried for 3 hours at 175° C.

Problems encountered with the melam so obtained are that dosing of the melam is difficult and preparation of flame retardant polymer compositions with homogenously dispersed melam therein is complicated. Grinding of the melam to sufficiently low particle size to enhance the dispersability results in low bulk density, thus causing high cost for transportation and storage. In addition this leads to a poor flow behavior. The melam obtained above is either too coarse or upon grinding comprises too many fine particles.

It is essential for the use of a flame retardant in flame retardant polymer compositions that the flame retardant be distributed as homogeneously as possible in the polymer. Such a homogeneous distribution is achieved in particular through good flow behaviour of the powder, whether or not combined with the break-up of agglomerate of the flame retardant into smaller particles upon addition to the polymer.

A similar problem is described in U.S. Pat. No. 7,547,738-B2 with respect to melamine cyanurate. This problem is claimed to be solved in U.S. Pat. No. 7,547,738-B2 so-called free flowing melamine cyanurate agglomerate containing melamine cyanurate aggregates with a small particle size 50 µm bonded to each other with the aid of a polymeric binding agent, referred to as auxiliary material. The said free flowing melamine cyanurate agglomerate is obtained by a process wherein melamine cyanurate aggregates are grinded to a small particle size and bonded with a polymeric binding agent, by combining the small particle size melamine cyanurate and the polymeric binding agent are combined in an aqueous slurry, the slurry is spray dried, the resultant agglomerates are collected, fine particles comprised by the agglomerates are separated and used in a new slurry and spray drying step.

In U.S. Pat. No. 7,547,738-B2 it is stated that the advantages mentioned for melamine cyanurate would also apply to agglomerates of other flame retardant compounds, including halogen containing and halogen-free ones, among the many of which melam is mentioned. However, the invention of U.S. Pat. No. 7,547,738-B2 was only based on examples with melamine cyanurate. It has been observed that if the process described above for melamine cyanurate was applied to melam obtained by the process described in WO 96/16948, still very fine and dusty material was obtained with a low bulk density and still hard to dose.

Granulate material with larger particle size could be obtained with melam by such process when a large amount of polymeric binding agent, well over 10 wt. %, relative to the amount of melam, was used. Such material was not considered suitable, because of the broad particle size distribution with too many fine and/or too many large particles, providing problem with dusting and/or dispersing during compounding processes. Furthermore, a large amount of polymeric binding agent can deteriorate the properties of the flame retardant polymer composition made by such compounding processes.

Therefore an aim of the invention is to provide a process for the preparation of a melam based flame retardant material that has better flow properties and compounding characteristics, and which does not have the disadvantages of the process described above. Another aim is to provide a melam based flame retardant material having such improved flow properties and high bulk density. A further aim of the invention is to provide a melam based flame retardant that shows improved compounding characteristics.

The invention provides a process for the preparation of a melam based granulate material, comprising steps of i. preparing an aqueous slurry from a freshly prepared moist melam having a water content of at least 8 wt. %, relative to the total weight of the moist melam, the slurry comprising water, melam and a water soluble polymeric binding agent, wherein the melam is present in an amount of 5-35 wt. % relative to the total weight of the slurry, and the water soluble polymeric binding agent is present in an amount of, 0.5-8 wt. % relative to the total amount of melam and the water soluble polymeric binding agent ii. drying the slurry in a fluid bed to form a granulate material; and iii. collecting the resulting granulate material.

The effect of the process according to the invention is that it results in a granulate material that has much better properties in respect of flowability and increased bulk density than a corresponding process starting from a pre-dried and grinded material as obtained by the process of WO 96/16948. The granulate material resulting from this process has good free flowing properties and has a reasonably relatively high bulk density.

The freshly prepared moist melam used in the process described above can be melam prepared by the process described in WO 96/16948 or any similar process, wherein the melam so produced may be separated from the reaction mixture, e.g. by filtration or decantation, and washed, but is not subjected to a drying step.

The aqueous slurry prepared from the freshly prepared moist melam, preferably comprises the melam in an amount of 5-25, more preferably 10-20 wt. %. Lower melam content will make the slurry better processable in the fluidized bed, whereas a higher content will make the process more economic. Too high melam content, such as above 35 wt. %, and in particular above 40 wt. %, results in a very bad product difficult to process if processable at all.

Once the melam obtained from the above production process is dried to a substantially extent, such as to a water content below 8 wt. %, and certainly to a water content below 4 wt. %, it becomes ever more difficult to obtain a granulated material, if not impossible at all, in particular when the melam is fully dried. In particular when the moist melam would be heated to elevated temperature, it will dry faster, and care should be taken that the moist melam is kept for not too long time at elevated temperature if any. As an indication fully dried melam, or lumps of fully dried melam next to moist melam, can already be obtained in about 5 hours at 60° C., in about 2 hours at 80° C., in about 1 hour at 100° C. and about 20 minutes at 120° C., which when used in the process according to the invention results in a bad granulation.

It is noted that the water in the freshly prepared moist melam may be present as either adherent water or as crystalline water or a combination thereof. In particular the melam in the freshly prepared moist melam may be present as a hydrate and/or semi-hydrate, likewise the hydrate and semi-hydrate being present in crystalline form.

The process according to the invention, wherein a freshly prepared moist melam is used in combination with a polymeric binding agent, may be carried out using standard operations and using standard operation units.

The drying step may be carried out by drying in a fluid bed. Preferably the slurry is dried in a fluid bed. The advantage is that the granulate material has a relatively narrow particle size distribution with a limited amount of (neither too many) fine particles and limited amount of (nor too many) coarse particles.

Drying in a fluid bed may be accomplished as follows. A fluid bed is created from powder, granules or droplets, by fluidization of the powder, granules or droplets in a stream of air, the fluid bed is maintained by the air stream, the aqueous slurry is injected into the fluid bed, granules are formed and grow inside the fluid bed and settle once reached sufficient size.

The water soluble polymeric binding agent may be added as a solid to the aqueous melam slurry. Alternatively, the polymeric binding agent is pre-dissolved in water and is added in the form of an aqueous solution.

The polymeric binding agent is suitably used in an amount in the range of 0.5-8 wt. %, relative to the total weight of the granulate material. Preferably, the amount is at most 6 wt. %, more preferably 5 wt. %, and even better at most 4 wt. %. Preferably the amount is at least 1 wt. %, and better at least 2 wt. %, relative to the total weight of the granulate material.

The softening point of the organic polymeric binding agent should not be so low as to make it possible for the polymeric binding agent to soften during storage, for example in a warm warehouse. This could cause the granules in the granulate material to adhere to one another. Therefore, the softening point of the organic polymeric binding agent will have to be higher than 40° C., preferably higher than 60° C., even more preferably higher than 80° C., especially for storage in tropical regions. This softening point can be either a glass transition temperature (Tg) in case the polymeric binding material is an amorphous polymer, or a melt temperature (Tm) in case the polymeric binding material is a semi-crystalline polymer.

Preferably the polymeric binding agent suitably is a water soluble or water dispersible polymeric material with a softening point of at least 100° C. More preferably, the polymeric binding material has a softening point of at least 150° C.

With the term glass transition temperature (Tg) is herein understood the temperature, measured according to ASTM E 1356-91 by DSC with a heating rate of 20° C./minute and determined as the temperature at the peak of the first derivative (with respect of time) of the parent thermal curve corresponding with the inflection point of the parent thermal curve. With the term melting temperature (Tm) is herein understood the temperature, measured according to ASTM D3418-97 by DSC with a heating rate of 20° C./min, falling in the melting range and showing the highest melting rate.

Suitable organic polymeric binding agents are organic compounds, polymers or copolymers based on vinyl alcohol, vinyl lactams, like vinylpyrrolidone and vinyl caprolactam, and vinyl acetate or mixtures thereof. Also suitable are polymers or copolymers based on epoxies, urethanes, acrylates, esters, amides, stearates, olefins, cellulose derivatives or mixtures thereof. Since the agglomerates are prepared from an aqueous slurry, water-soluble organic polymeric binding agents are of advantage because they can easily be added to this slurry, either as such or in the form of an aqueous solution of the polymer.

Also preferably the polymeric binding agent comprises a polymeric material chosen from the group consisting of polyvinyl alcohol, ethylene vinyl alcohol copolymers, polyvinyllactams and copolymers of vinyllactam and other vinyl monomers. Preferably, the polymeric binding agent comprises polyvinyl alcohol, polyvinylpyrrolidone and/or polyvinylcaprolactam. Polyvinyl pyrrolidone, polyvinyl alcohol and polyvinyl caprolactam are easy to handle and can be used in a wide range of applications due to their good solubility in water and compatibility with many polymers. More preferably the polymeric binding agent comprises or even consists of polyvinylpyrrolidone.

The advantage of using polyvinylpyrrolidone as a polymeric binding agent in the granulate preparation process according to the invention, is that the drying of the melam granulate goes much faster compared to the wet melam cake obtained as such from the melam production process. Suitably, the polyvinylpyrrolidone has a weight average molecular weight (Mw) in the range of 9-1500 kg/mole, and preferably in the range of 20-1000 kg/mol. Furthermore, polyvinylpyrrolidone with an Mw of at least 30 kg/mol is highly suitable for use in polymers with high glass transition temperature (Tg) or high melting temperature (Tm).

The process suitably comprises a step wherein fine and/or coarse granules, which might eventually be present, although typically in small amounts only, are removed by a classification step inside or outside the fluid bed, for example by using a cyclone to remove fine particles and/or a sieve to remove coarse particles. Although the amount of fine particles and coarse granules in the granulate material resulting from the process is already low, the amount can be further reduced by such classification step.

The process according to the invention seems to provide for a more intimate distribution of the polymeric binding agent between primary particles rather than binding multiple primary particles by a covering layer. Overall, irrespective whether due to this phenomenon or other aspects, the process results in granulate material with interesting properties.

The granulate material obtained by the process according to the invention does not need to be fully dried to achieve the so desired free flowing properties. For that purpose it is sufficient to dry the granulate material to a water content of at most 12 wt. %, relative to the total weight of the granulate material. Suitably, the granulate material is dried to a water content of 0-12 wt. %, preferably 1-10 wt. %, more preferably 2-8 wt. %. Most conveniently the water content is about 4-6 wt. %, relative to the total weight of the granulate material. It has been observed that the residual water in the granulate material does not hamper the free flowing properties of the granulate material and even smoothens the compounding process used for making polymer compositions comprising melam as a flame retardant.

The invention also relates to a melam granulate material. The melam granulate material according to the invention is a granulate material, obtainable by the process according to the invention, comprising melam, 0.5-8 wt. % of a polymeric binding agent and 0-12 wt. % of water, wherein the wt. % are relative to the total weight of the granulate material, and wherein the granulate material consists of granules with a median particle size (d50) in the range of 100-1000 μm and comprises melam particles bonded to each other with the polymeric binding agent, and the granulate material has a Carr-P bulk density of at least 400 kg/m$^3$. The said granulate material has good free flowing properties as described above, and can be easily dispersed in polymer compositions by melt compounding processes. This in contrast with the granulate material obtained from a similar process but starting from predried melam, which granulate has a large content of fines, a very low bulk density, is not free flowing and difficult to disperse homogeneously in by melt compounding processes.

The granulate material according to the invention preferably comprises water in an amount of 1-10 wt. %, more preferably 2-8 wt. %, and most conveniently about 4-6 wt. %, relative to the total weight of the granulate material.

The amount of water in the granulate material is not very critical for the free flowing characteristics, as long as it stays within the general range of 0-12 wt. %. A lower maximum amount has the advantage that less water has to be released during compounding, thereby reducing the risk of carrying away other components. A higher minimum amount has the advantages that the drying process upon preparation of the granulate material can be shortened. Furthermore, for the presence of the water helps to reduce the melt peak temperature required during a melt mixing process for preparing flame retardant compositions.

The organic polymeric binding agent binds the melam particles in the granules to each other. However, the organic polymeric binding agent should not bind together the aggregates and/or primary melam particles so strongly that the agglomerates no longer disperse in the polymer. This can be achieved by using a lower amount of polymeric binding agent and by selecting the polymeric binding agent in function of the type of process or the process conditions in which the melam granulate is added to the polymer, and/or the compatibility with the polymer. In the case of processing in a polymer melt, the choice of polymeric binding agent can be determined by the softening point of the organic polymeric binding agent and the temperature of the polymer melt. The softening point of the organic polymeric binding agent is chosen so that it is lower than the temperature of the polymer melt to which the melam granulate is added, but also not too far below said polymer melt temperature in order to prevent premature melting and sticking of the granulate in the hopper feeder or in the dosing channels. Since melam is in particular of interest for use as flame retardant in high melting polymers involving high processing temperatures, it is also preferred to have a organic polymeric binding agent with a high softening point as binding agent in the melam granulate. An added advantage is that the granulate material according to the invention better retains its free-flowing properties and improved bulk density during handling and storage. As a result, the agglomerates can be dosed to a polymer in a very constant manner and a very homogeneous distribution of the melam in the polymer is achieved.

The polymeric binding agent suitably comprises any of the polymeric binding agents described above, of which preferably polyvinyl alcohol, polyvinylpyrrolidone and/or polyvinylcaprolactam, and more preferably polyvinylpyrrolidone.

The granulate material according to the invention, and which is obtainable by the process according to the invention, has a granule particle size and granule particle size distribution and a bulk density which apparently are appropriate to provide for the free flowing characteristics.

Generally, the bulk density is in the range of 400-1000 kg/m$^3$, and the median particle size (d50) in the range of 100-1000 μm. The bulk density of the melam granulate is not critical, but preferably lies between 450 and 700 kg/m$^3$. This results in better flow properties, which also enables regular dosing into the polymer melt, and makes it easier to achieve good mixing with other polymers. The bulk density is herein understood to be the density, measured by the Carr test as defined in ASTM D 6393-08 on tapped material, which density is also referred to as Carr-P bulk density.

Preferably the median particle size (d50) of the melam granulate material is in the range of 200-900 μm, more preferably 400-850 μm. With d50 is herein meant the particle size relative to which 50 wt. % of the particles has a smaller or equal particle size, and 50 wt. % of the particles has a larger particle size. Herein the wt. % is relative to the total weight of the granulate material.

It has been observed that the granulate material with a d50 of at most 900 μm still has a relatively high density and good flow properties, and shows very good compounding characteristics. At the same time, it is preferred to have a d50 of at least 200 μm. This has the advantage that the number of fines and related dusting problems are limited.

It is also preferred that the granulate material has a d10 of at least 10 μm, more preferably at least 25 μm and/or a d90 of at most 3000 μm, more preferably at most 2000 μm, and even better at most 1500 μm. With d10 is herein meant the particle size relative to which 10 wt. % of the particles has a smaller or equal particle size, and 90 wt. % of the particles has a larger particle size. Analogously, with d90 is herein meant the particle size relative to which 90 wt. % of the particles has a smaller or equal particle size, and 10 wt. % of the particles has a larger particle size. Also preferably, a fraction of granulate particles measuring less than 50 μm amounts to less than 20 wt. %. More preferably, this fraction amounts to less than 10 wt. %, even more preferably to less than 5 wt. %. Granulate material containing a smaller amount of particles of a size below 50 μm cause less dusting problems during handling or when they are dosed to a polymer melt. Also, the flow behaviour of the granulate material is improved.

The average or mean particle size of the granulate material can be steered by varying the concentration of the solid content, i.e. total amount of melam and water soluble polymeric binding agent, in the aqueous slurry. In spray drying a higher concentration generally leads to larger granules, while a lower concentration generally leads to smaller particles. However, with spray drying this could lead too easily to too many coarse or too many fine particles, requiring an additional external classification step, being either by sieving or by using a cyclone.

The melam particles in the granulate material, which may consist of primary particles and/or agglomerates of small crystals, suitably have a median particle size (d50) in the range of 0.1-50 μm, preferably 1-25 μm.

The flow behaviour was judged from the compressibility. The compressibility is calculated according to ASTM D 6393-08 from the L and P-density measured in the Carr test on the Hosokawa powder tester. The compressibility is expressed as: $((P-L)/P)*100\%$. With regard to flow behaviour, the agglomerates according to the invention have a compressibility of typically at most 20%, in many cases at most 15% or even at most 10%. According to ASTM D 6393-08, a material with compressibility less than 10% is considered a very good flowing material.

The invention also relates to the use of the melam granulate material for the preparation of a flame retardant polymer composition. The invention in particular relates to such use wherein the melam granulate material is used in a melt mixing process and added to the melt of a thermoplastic polymer for the preparation of a flame retardant polymer composition comprising melam and the thermoplastic polymer.

The invention further relates to a flame retardant polymer composition obtained by a process wherein the melam granulate material according to the invention is used.

The invention in particular relates to a flame retardant polymer composition comprising a thermoplastic polymer, melam and the polymeric binding agent as described above. Suitably, the polymeric binding agent is herein present in an amount of 0.5-8 wt. %, relative to the total weight of the polymeric binding agent and the melam.

The thermoplastic polymer may be an amorphous polymer or a semicrystalline polymer. The thermoplastic polymer may be chosen, for example, from polyesters, polyamides, polycarbonates, polyetheretherketons, polyphenylene ethers, polyphenylene sulfides, and polyethyleneimides.

The thermoplastic polymer suitably is a polymer with a softening point of at least 260° C., preferably at least 280° C., more preferably at least 300° C., and suitably up to and even above 350° C. In case the polymeric material is an amorphous polymer, the softening point is determined by a glass transition temperature (Tg) can be either a glass transition temperature (Tg) in case the polymeric material is a semi-crystalline polymer, the softening point is determined by a melt temperature (Tm).

In a preferred embodiment, the flame retardant polymer composition comprises a thermoplastic polyamide, melam and a polylactam as the polymeric binding agent. Preferably, the polymeric binding agent herein comprises polyvinyl alcohol, polyvinylpyrrolidone and/or polyvinylcaprolactam. More preferably, the polymeric binding agent herein is polyvinylpyrolidone.

The invention is further illustrated with the following examples and comparative experiments.

Materials

Melamine (ex. DSM)

P-1 Luvitec k17 (ex BASF) PVP, $M_w$ 9 kg/mol, $M_n$ 2 kg/mole, $T_g$ 100° C. measured on dry PVP containing no water, Moisture uptake at 23° C., 75% RH 40 wt %.

P-2 Luvitec k30 (ex BASF) PVP, $M_w$ 50 kg/mole, $M_n$ 14 kg/mole, $T_g$ 175° C. measured on dry PVP containing no water, Moisture uptake at 23° C., 75% RH 40 wt %.

P-3 Luvitec k90 (ex BASF) PVP, $M_w$ 1400 kg/mole, $M_n$ 325 kg/mole, $T_g$ 180° C. measured on dry PVP containing no water, Moisture uptake at 23° C., 75% RH 40 wt %.

P-4 Luvitec VA64p (ex BASF) PVP-PVA copolymer, $M_w$ 65 kg/mole, $M_n$ 15 kg/mole, $T_g$ 105° C. measured on dry PVP-PVA copolymer containing no water, Moisture uptake at 23° C., 75% RH 15 wt %.

Methods

Particle Size

The particle size was measured with a high speed image analysis sensor using a Sympatec Qicpic particle sizer equipped with a disperser and image processing. The Qicpic takes images in a flow of moving particles and enlarges the sample size. The particles show arbitrary orientation and the number of overlapping particles is reduced. This method is most suitably applied for granulate with an average particle size of more than 100 μm:

Density

The density is measured by the Carr test as defined in ASTM D 6393-08. For the test a Hosokawa powder tester was used. The density was measured on loosely filled material, referred to as Carr loose density (L) and respectively on tapped material, referred to as Carr tapped density (P), or Carr-P bulk density.

Flow Behaviour

The flow behaviour was judged from the compressibility. The compressibility is calculated according to ASTM D 6393-08 from the L and P-density measured in the Carr test on the Hosokawa powder tester. The compressibility is expressed as: $((P-L)/P)*100\%$. According to ASTM D 6393-08, a material with compressibility less than 10% is considered a very good flowing material.

Process Description

Moist Melam

Melam was prepared by the process as described in WO 96/16948, wherein melamine was heated in the presence of p-toluene sulfonic acid at a temperature between 300 and 315° C. The resulting product was treated with an ammonia solution. A precipitate was formed which was filtered of to form a moist cake. The moist cake was washed several times with a 3% ammonia solution to remove residual p-toluene sulfonic acid traces. The resulting wet cake contained about 40 wt % solids, and was used as such for the further experiments Dry Melam An amount of the washed moist melam cake was dried for 3 hours at 175° C., thereby resulting in dry melam. The dried melam was grinded to a granulate material with an average particle size of about 25 μm.

EXAMPLE 1

Melam wetcake containing 40 wt % solids was diluted with water to form aqueous melam slurry of 15 wt % (solids). The slurry was stirred using a mechanical stirrer and heated to 50° C., during which P-1 powder was slowly added in an amount of 3.5 wt % on melam basis. The slurry was dosed to a Glatt GPCG-3 fluid bed setup. The operation mode of the fluid bed was in bottom spray mode. The temperature conditions in the fluid bed were 80° C. The fluid bed was initially filled with seeds (nuclei) of melam of about 75% undersize. The slurry is sprayed on the nuclei which grow until the process reached a steady state, wherein the granulate growth was stabilized.

EXAMPLES 2-4

These examples were carried out in the same as above for example 1, except that P-1 was replaced by P-2, P-3 and P-4 respectively.

EXAMPLE 5

This example was carried out in the same as above for example 3, with P-3, except that it was done in a continuous fluid bed setup allowing for internal classification. The internal classification system of the fluid bed allowed the granules larger than 800 μm to be discharged whereas the smaller granules are retained in the fluid bed. The results for the particle size measurement of the granulate after classification are shown in Table 1.

TABLE 1

Typical particle size of the granules after classification

| Cumulative undersize (wt. %) | Size (μm) |
|---|---|
| $d_{10}$ | 550 |
| $d_{50}$ | 750 |
| $d_{90}$ | 1032 |
| Span = $(d_{90} - d_{10})/d_{50}$ | 0.6 |

COMPARATIVE EXPERIMENT A

This Comparative Experiment was carried out in the same as above for example 5, with P-3, in the continuous fluid bed setup with internal classification, except that instead of wet melam, pre-dried and grinded melam was used.

Sieve Test

The products of Example 5 and Comparative Experiment A were subjected to a sieve test, where small particles were separated by sieves and the amount of particles larger than 100 μm was determined. The results are indicated in Table 2.

TABLE 2

Granulation efficiency for Example 5 and Comparative Experiment A

| Experiment | Melam source/ PVP type | Granulation efficiency (wt %) |
|---|---|---|
| Ex-5 | Moist melam cake/P-3 | 30 |
| CE-A | Dried melam/P-3 | 2 |

It appeared from these results that the granulation behaviour of freshly prepared moist melam is much better compared to pre-dried melam. Granulation efficiency is defined as the weight fraction particles larger than 100 μm compared to the total sample of melam.

COMPARATIVE EXPERIMENT B

This Comparative Experiment was carried out in the same as above for example 3, except that the slurry was spray dried in a spray drying setup.

Test Results on Examples 3 and 4 and Comparative Experiment B

Particle size and flowability according to Carr compressibility of the granulate of Examples 3 and 4 and Comparative Experiment B were compared. The test results have been collected in Table 3.

TABLE 3

Test results on Examples 3 and 4 and Comparative Experiment B

| Experiment | PVP type | D50 (μm) | Span (—) | L (kg/m$^3$) | P (kg/m$^3$) | Flowability |
|---|---|---|---|---|---|---|
| Ex 3 | P-3 | 766 | 0.5 | 433 | 460 | Very good |
| Ex 4 | P-4 | 782 | 0.5 | 434 | 472 | Very good |
| CE-B | | 25 | 14 | 280 | 400 | Not good |

The flowability of the granulate clearly increases upon granulation in the process according to the invention.

EXAMPLE 6-9

Experiment 2 was repeated 4 times. A freshly produced melam wetcake containing 43 wt % solids was diluted with water to form an aqueous melam slurry of 20 wt % (solids). The slurry was stirred using a mechanical stirrer and heated to 50° C., during which P-2 powder was slowly added in an amount of 3.5 wt % on melam basis. The slurry was dosed to a Glatt AGT400 ($T_{air,\ inlet}$=195° C.; $T_{bed}$=60° C.) continuous fluid bed setup. The fluid bed was initially filled with seeds (nuclei) of melam of about 75% undersize. The slurry is sprayed on the seeds which grow until the process reached a steady state, wherein the granulate growth was stabilized.

COMPARATIVE EXPERIMENT C-F

As comparative experiments the same experiment was carried out four times, as above for examples 6-9, with P-2, in the continuous fluid bed setup, except that instead of wet melam, pre-dried melam powder was used.

The results of Examples 6-9 and Comparative Experiments C-F are shown in Table 4.

TABLE 4

Results of Examples 6-9 and Comparative Experiments C-F

| Experiment | PVP type | D50 (um) | Span (—) | L (kg/m3) | P (kg/m3) | Flowability |
|---|---|---|---|---|---|---|
| Ex 6 | P-2 | 810 | 0.75 | 432 | 508 | Very good |
| Ex 7 | P-2 | 795 | 0.77 | 399 | 499 | Very good |
| Ex 8 | P-2 | 816 | 0.86 | 461 | 512 | Very good |
| Ex 9 | P-2 | 799 | 0.88 | 428 | 503 | Very good |
| CE-C | P-2 | 41 | 17.9 | 232 | 309 | Not good |
| CE-D | P-2 | 37 | 19.8 | 205 | 316 | Not good |
| CE-E | P-2 | 42 | 17.5 | 248 | 341 | Not good |
| CE-F | P-2 | 40 | 18.4 | 221 | 320 | Not good |

The results show a very good reproducibility for both the Examples and the comparative Experiments. Moreover, the Examples 6-9 show a large mean particle size (d50) and a relatively narrow particle size distribution (low Span value), indicative for a low amount of fines, a high P-Carr density and a very good flow behavior. The comparative Experiments C-F show a small mean particle size (d50) and a relatively wide particle size distribution (high Span value), indicative for a large amount of fines next to large particles, a low P-Carr density and a bad flow behavior.

The invention claimed is:

1. A process for the preparation of a melam granulate material, the process comprising steps of:
   (i) preparing an aqueous slurry from a freshly prepared moist melam having a water content of at least 8 wt. %, relative to the total weight of the moist melam, the slurry comprising water, melam and a water soluble polymeric binding agent, wherein the melam is present in an amount of 5-35 wt. % relative to the total weight of the slurry, and the water soluble polymeric binding agent is present in an amount of 0.5-8 wt. % relative to the total amount of melam and the water soluble polymeric binding agent;
(ii) drying the slurry in fluid bed to form a granulate material consisting of granules comprised of melam particles bonded to each other with the polymeric binding agent, wherein the granules have a median particle size (d50) in a range of 100-1000 µm; and
(iii) collecting the resulting granulate material.

2. The process according to claim 1, wherein step (ii) comprises drying the granulate material to a water content of at most 12 wt. %, relative to the total weight of the granulate material.

3. The process according to claim 2, wherein step (ii) comprises drying the granulate material to a water content of 0-6 wt. %, relative to the total weight of the granulate material.

4. The process according to claim 1, wherein the median particle size (d50) of the granules is in the range of 200-900 µm.

5. The process according to claim 1, wherein the granulate material has a mean particle size (d10) of at least 10 µm and/or a mean particle size (d90) of at most 3000 µm.

6. The process according to claim 1, wherein the amount of the polymeric binding agent is in the range of 1-6 wt. %, relative to the total weight of the granulate material.

7. The process according to claim 1, wherein the polymeric binding agent is at least one selected from the group consisting of polyvinyl alcohol, polyvinylpyrrolidone and polyvinylcaprolactam.

8. The process according to claim 1, wherein the melam particles of the granulate material have a median primary particle size (d50) in a range of 0.1-50 µm.

9. The process according to claim 1, wherein the granulate material obtained in step (ii) has a Carr-P bulk density in the range of 400-1000 kg/m$^3$.

* * * * *